United States Patent [19]

Schoner et al.

[11] Patent Number: 5,192,669
[45] Date of Patent: Mar. 9, 1993

[54] METHOD TO PRODUCE RECOMBINANT PROTEINS USING AN EXPRESSION VECTOR COMPRISING TRANSCRIPTIONAL AND TRANSLATIONAL ACTIVATING SEQUENCES

[75] Inventors: Brigitte E. Schoner; Ronald G. Schoner, both of Monrovia, Ind.

[73] Assignee: Eli Lilly and Company, Indianapolis, Ind.

[21] Appl. No.: 744,612

[22] Filed: Aug. 13, 1991

Related U.S. Application Data

[60] Division of Ser. No. 449,199, Dec. 12, 1989, Pat. No. 5,063,158, which is a continuation-in-part of Ser. No. 118,678, Nov. 9, 1987, abandoned.

[51] Int. Cl.$^5$ .................. C12P 21/06; C12N 1/20; C12N 15/00
[52] U.S. Cl. ...................... 435/69.4; 435/69.1; 435/252.31; 435/252.35; 435/252.33; 435/320.1; 935/44
[58] Field of Search ............... 435/69.1, 252.3, 252.33; 935/44, 45, 6, 8

[56] References Cited

U.S. PATENT DOCUMENTS

4,693,973  10/1987  Buell et al. ......................... 435/68
4,806,471  2/1989  Molin et al. .

FOREIGN PATENT DOCUMENTS

2073245A  3/1981  European Pat. Off. .
0095361  5/1983  European Pat. Off. .
1557774  5/1978  United Kingdom .

OTHER PUBLICATIONS

Miller et al., 1980, The Journal of Biological Chemistry 255(16):7521.
Martial et al., 1979, Science 205:602.
Seeburg et al., 1983, DNA 2(1):37.
Masiu et al., The International Journal of Biology and Industry, Jan. 1984:81.
Movva et al., 1980, Proceedings of the National Academy of Science 77(7):3845.
Schoner et al., 1984, Proceedings of the National Academy of Science 81:5403.
Iserentant et al., 1980, Gene, 9:1.
Jay et al., 1981, Proc. Natl. Acad. Sci. USA 78(9):5543.
Shepard et al., 1982, DNA 1(2):125.
Gheysen et al., 1982, Gene, 17:55.
Kastelein et al., 1983, Gene, 23:245.
Hui et al., 1984, The EMBO Journal, 3(3):623.
Tessier et al., 1984, Nucleic Acids Research, 12(20):7663.
Stanssens et al., 1985, Gene, 36:211.
Marquis et al., 1986, Gene, 42:175.

Primary Examiner—Jacqueline Stone
Assistant Examiner—Deborah Crouch
Attorney, Agent, or Firm—John E. Parrish; Leroy Whitaker

[57] ABSTRACT

The present invention is composed of novel recombinant DNA expression vectors which contain a transcriptional activating sequence, a translational activating sequence and a DNA sequence coding for a functional polypeptide, especially bovine growth hormone. The aforementioned translational activating sequences contain a ribosome binding site and are designed to provide high level expression of DNA that codes for virtually any functional polypeptide. The invention further provides transformed microbial host cells capable of producing bovine growth hormone and other functional polypeptides at high levels.

28 Claims, 11 Drawing Sheets

Plasmid 103 (Figure 1)
↘ HindIII
↘ S1 Nuclease
↘ BamHI Linkers
↘ T₄ DNA Ligase
↘ BamHI
↘ T₄ DNA Ligase ↙ EcoRI Partial Digestion
↙ S1 Nuclease
↙ HindIII Linkers
  T₄ DNA Ligase
↙ HindIII
↙ T₄ DNA Ligase

Restriction Site Map of Plasmid pCZ101

Restriction Site Map of Plasmid pCZ118

Restriction Site Map of Plasmid pCZ145**

METHOD TO PRODUCE RECOMBINANT PROTEINS USING AN EXPRESSION VECTOR COMPRISING TRANSCRIPTIONAL AND TRANSLATIONAL ACTIVATING SEQUENCES

CROSS-REFERENCE TO RELATED APPLICATIONS

This application is a division of application Ser. No. 07/449,199, filed Dec. 12, 1989, now U.S. Pat. No. 5,063,158, which is a continuation-in-part of application Ser. No. 07/118,678, filed Nov. 9, 1987, now abandoned.

BACKGROUND AND SUMMARY OF THE INVENTION

The present invention is a novel selectable and autonomously replicating recombinant DNA expression vector which contains 1) a transcriptional and translational activating nucleotide sequence, 2) a gene that codes for a bioactive derivative of bovine growth hormone (bGH) and 3) a replicon which, under induced conditions, loses copy number control. The invention further contains novel transformants of the aforementioned vectors, bovine growth hormone derivatives and methods of use.

The development and exploitation of recombinant DNA technology for the production of bGH has been severely handicapped by problems of gene expression. Some of these problems, detailed in European Patent Application Publication No. 0075444, involve the transcription of functionally suboptimal mRNA.

The development and exploitation of recombinant DNA technology has been limited by the general of vectors providing for high levels of gene expression. Although the lac (Roberts et al., 1979, Proc. Nat. Acad. Sci. USA 76:5596 and Guarante et al., 1980, Cell 20:543), trp (Hallewell and Emtage, 1980, Gene 9:27), bacteriophage λ $P_L$ (Remaut et al., 1981, Gene 15(1):81, Bernard et al., 1979, Gene 5:59 and Derom et al., 1982, Gene 17:45) and lpp (Ziebel et al., 1981, J. Bacteriol. 145:654, Lee et al., 1981, J. Bacteriol. 146:861 and Nakamura and Inouye, 1979, Cell 18:1109) promoter systems have been incorporated into assorted recombinant DNA vectors, few, if any, other expression systems are available. In fact, many heterologous genes are not expressed or are, at best, only poorly expressed using these known expression vectors. Such failure of expression is frequently associated with the transcription of a mRNA that is sub-optimal or incapable of binding to ribosomes. This may be due to the formation of inappropriate stem and loop structures that sequester sites for ribosome binding or to the presence of sequences that inhibit ribosome binding or initiation of translation. Some of these problems are further described in European Patent Application Publication No. 0075444.

The present invention solves problems of expression without requiring the synthetic modification of a gene. Such synthetic modification is not only time consuming and costly but also substantially increases the risk of accidentally introducing errors into a DNA sequence. This problem is circumvented in the present invention by altering the 5' end of a mRNA transcript without modifying or changing the sequence of a particular gene of interest.

For purposes of the present invention as disclosed and claimed herein, the following terms are as defined below.

Recombinant DNA Cloning Vector—any autonomously replicating agent, including but not limited to plasmids, containing a DNA molecule to which one or more additional DNA segments can or have been added Recombinant DNA Expression Vector—any recombinant DNA cloning vector into which one or more transcriptional and translational activator sequence(s) have been incorporated.

Transcriptional Activating Sequence—any DNA sequence that directs or provides for the transcription of DNA into a mRNA transcript.

Translational Activating Sequence—any DNA sequence that directs or provides for the translation of a mRNA transcript into a peptide, polypeptide or protein.

Translational Start Signal—any DNA triplet that codes for a translational start codon.

Translational Stop Signal—any DNA triplet that codes for a translational stop codon.

Transformation—the introduction of DNA into a recipient host cell.

Transformant—a recipient host cell that has undergone transformation.

Restriction Fragment—any linear DNA sequence generated by the action of one or more restricton enzymes.

Functional Polypeptide—a recoverable biologically active homologous or heterologous polypeptide or precursor, a recoverable polypeptide containing a heterologous polypeptide and a portion or whole of a homologous polypeptide, or a recoverable bioinactive fusion polypeptide containing a heterologous polypeptide and a bio-inactivating polypeptide which can be specifically cleaved.

Fused Gene Product—a recoverable heterologous polypeptide which contains a portion or whole of a homologous polypeptide.

Replicon—any DNA sequence that controls the replication of recombinant DNA cloning and expression vectors.

Runaway Replicon—a replicon which lacks or can be induced to lose copy number control, such loss resulting in the uncontrolled replication and an extreme increase in the copy number of DNA into which such replicon has been incorporated.

DETAILED DESCRIPTION

Figure 1:
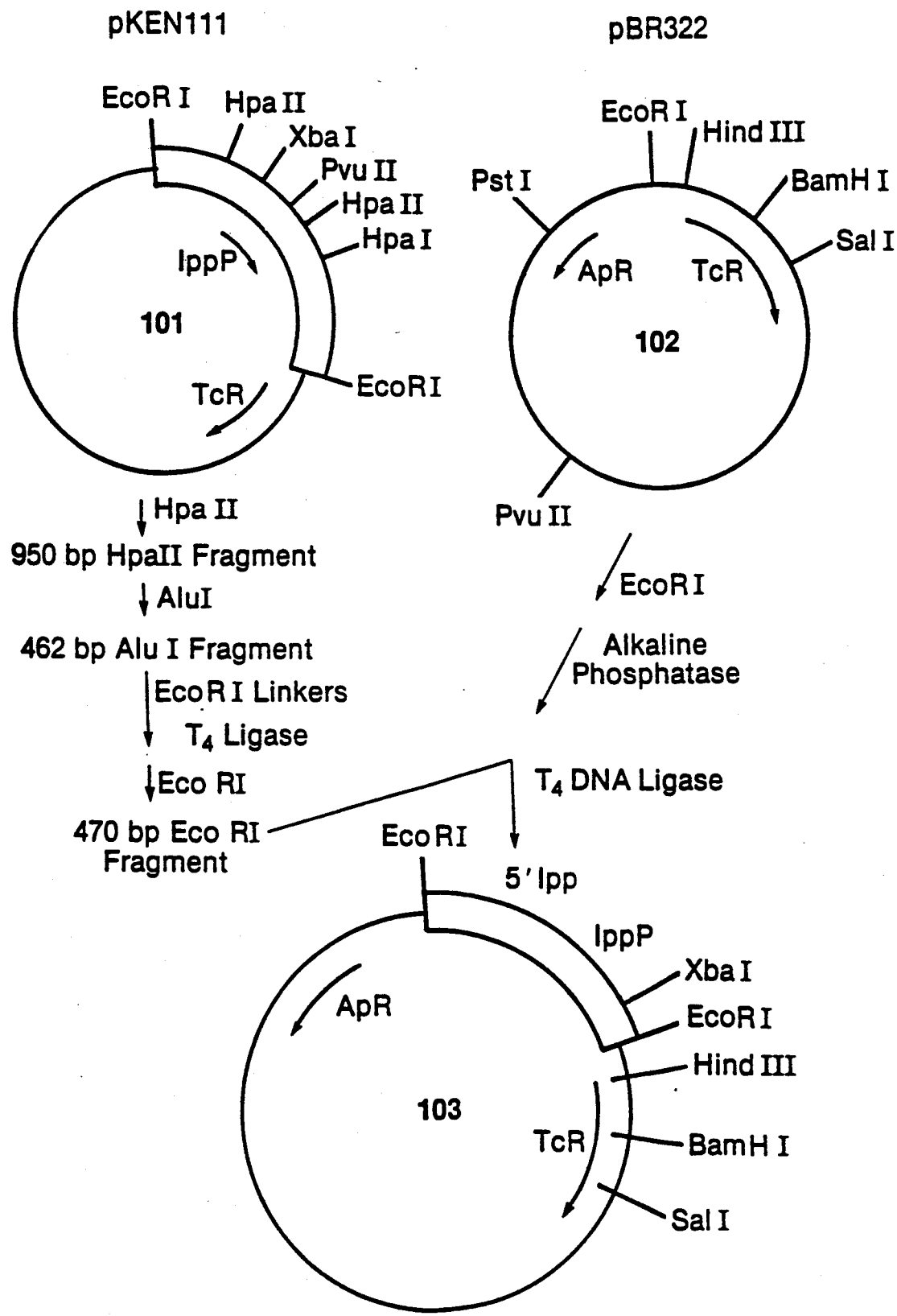
FIGS. 1-4—Schematic illustration of the construction protocol for plasmid pNM575.

The present invention contains a novel recombinant DNA expression vector which sequentially contains
 a) a transcriptional activating sequence,
 b) a translational activating sequence selected from the group consisting of 1) 5'-CTAGAGGGTATTAATAATCTATCGATTA
   3'-    TCCCATAATTATTAGATAGCTAAT
   AATAAGGAGGAATAACA   -3'
   TTATTCCTCCTTATTGTAT-5'

2) 5'-CTAGAGGGTATTAATAATCTATCGATTT
   3'-    TCCCATAATTATTAGATAGCTAAA
   AAATAAGGAGGAATAACA   -3'
   TTTATTCCTCCTTATTGTAT-5'

3) 5'-CTAGAGGGTATTAATAATCTATCGATTT
   3'-    TCCCATAATTATTAGATAGCTAAA
   AAAAAAGGAGGAATATAA   -3'
   TTTTTTCCTCCTTATATTAT-5'

4) 5'-CTAGCGATTAAATAAGGAGGAATAACA   -3'
   3'-    GCTAATTTATTCCTCCTTATTGTAT-5'

5) 5'-CTAGCGGATCCGCGATTAAATAAGGAGG
   3'-    GCCTAGGCGCTAATTTATTCCTCC
   AATAACA   -3'
   TTATTGTAT-5'

6) 5'-CTAGCGTTAACGCGATTAAATAAGGAGG
   3'-    GCAATTGCGCTAATTTATTCCTCC
   AATAACA   -3'
   TTATTGTAT-5'

7) 5'-CTAGCGATTTAAATAAGGAGGAATAACA   -3'
   3'-    GCTAAATTTATTCCTCCTTATTGTAT-5' and 8) 5'-CTAGCGGGATCCCGCGATTTAAATAAGG
   3'-    GCCCTAGGGCGCTAAATTTATTCC
   AGGAATAACA   -3'
   TCCTTATTGTAT-5' wherein
A is deoxyadenyl,
G is deoxyguanyl,
C is deoxycytidyl,
T is thymidyl, and
c) a DNA sequence that codes for a functional polypeptide with a methionine as the first amino acid at the amino-terminus;
subject to the limitation that sequences a and b are positioned for microbial expression of sequence c.

The invention further contains DNA sequences employed to construct the above vectors as well as transformed host cells containing such sequences and vectors.

The present invention is constructed by ligating either the a1, a2, a3, a4, a5, a6, a7, or a8 XbaI-NdeI DNA linker sequence into the ~g 2 kb XbaI-NdeI fragment of pCZ145. The resulting plasmids, designated pCZ149, pCZ183, pCZ184 pCZ149.1 pCZ149.2, pCZ149.3, pCZ183.1, and pCZ183.2, respectively, sequentially contain 1) the E. coli lipoprotein gene transcriptional activating sequence (Nakamura and Inouye, 1979), 2) a translational activating sequence, 3) a translational start signal which is in the reading frame of a nucleotide sequence coding for methionyl-bovine growth hormone (met-bGH) and 4) a translational stop signal appropriately positioned and in the reading frame of the met-bGH coding sequence.

The plasmid pCZ145 starting material is ~9.2 kb and is constructed by ligating the XbaI-HgiAI DNA linker sequence:

5'-CTAGAGGGTATTAATA ATG TAT CGA TTA AAT AAG GAG GAA TAA
3'-    TCCCATAATTAT TAC ATA GCT AAT TTA TTC CTC CTT ATT

CAT ATG GCT TTC CCA GCC ATG TCC TTG TCC GGC CTG TTT GCC
GTA TAC CGA AAG GGT CGG TAC AGG AAC AGG CCG GAC AAA CGG

AAC GCT GTG CT-3'
TTG CGA C    -5' into the 0.6 kb BamHI-HgiAI and 8.6 kb BamHI-XbaI fragments of plasmid pCZ118.

The plasmid pCZ118 is ~9.2 kb and is constructed by deleting the ~1.6 kb EcoRI-NdeI fragment from plasmid pCZ101. The plasmid pCZ101 is ~10.8 kb and is constructed by ligating the 0.6 kb XbaI-BamHI fragment of plasmid pNM789B into similarly digested plasmid pIM-I'-A3.

The latter plasmid, which contains the transcriptional and translational activating sequence of the E. coli lipoprotein gene and a thermoinducible runaway replicon, can be obtained from E. coli K12 RV308/pIM-I'-A3, a strain deposited and made part of the permanent stock culture collection of the Northern Regional Research Laboratory, Peoria, Ill. The strain is available as a preferred source and stock reservoir of the plasmid under the accession number NRRL B-15733. The plasmid pNM789B starting material is derived from plasmid pKEN111 in accordance with the steps illustrated and described in FIGS. 1–8 and Example 1 below. Plasmid pKEN111 can be obtained from E. coli K12 CC620/pKEN111, a strain deposited and made part of the permanent stock culture collection of the Northern Regional Research Laboratory, Peoria, Ill. The strain is available as a preferred source and stock reservoir of the plasmid under the accession number NRRL B-15011. Plasmid pNM789B also contains the transcriptional and translational activating sequence of the E. coli lipoprotein gene and, in addition, the coding sequence, including an appropriately positioned translational stop signal, for a fusion protein comprising bGH and a nine member polypeptide at the bGH N-terminus. Ligation of the aforementioned transcriptional activating and fusion protein-coding sequence, contained in the XbaI-BamHI fragment, to appropriately cleaved plasmid pIM-I'-A3 results in the aforementioned plasmid pCZ101 starting material.

Many related bGH expression plasmids which further exemplify the present invention can also be constructed. For example, although a particular DNA linker sequence must allow for the expression of a polypeptide from a mRNA transcript, the number of linker DNA sequences that can be used for such constructions is virtually limitless. These sequences can be conventionally synthesized by the modified phosphotriester method using fully protected dideoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765.

The present invention is in no way limited to the use of a particular transcriptional activating sequence since the choice of a specific sequence is not critical to the operability of the present invention. Transcriptional activating sequences which can be substituted for the previously exemplified lipoprotein activating sequence include, but are not limited to, the *E. coli* tryptophan (trp), *E. coli* lactose (lac), bacteriophage λ $P_LO_L$, bacteriophage λ $P_RO_R$, *Bacillus subtilis* vegetative (veg) (Miller et al., 1985, J. Bacteriol 162:521), and transcriptional activating sequences from Streptomyces. In addition, one or more transcriptional activating sequences can be used in tandem, such as, for example, the trp and lac transcriptional activating sequences. All of the aforementioned sequences have been previously characterized and can be constructed either synthetically or from known plasmids.

The present invention is highly versatile such that virtually any nucleotide sequence that codes for a functional polypeptide can be substituted for the met-bGH coding sequence exemplified above. Such coding sequences include, but are not limited to, sequences that code for human growth hormone (hGH), human pre-growth hormone (pre-hGH), porcine growth hormone (pGH), mammalian growth hormone, avian growth hormone, human growth hormone releasing-factor, bovine or porcine growth hormone releasing-factor, human insulin A chain, human insulin B chain, human proinsulin, human and non-human interferon, urokinase, tissue plasminogen activator, interleukin I and II, any polypeptide hormone, any enzyme and any functional polypeptide of research or commercial value. More particularly, an illustrative vector wherein the functional polypeptide hGH can be constructed by ligating both the ~10.2 kb BamHI-XbaI fragment of plasmid pCZ101 and the ~0.5 kb BamHI-FnuDII fragment of plasmid pNM575 into any of the linker sequences 1, 2, 3, 4, 5, 6, 7, or 8 shown above.

In the specific embodiments herein described, plasmid replication is determined by a thermoinducible runaway replicon disclosed in both GB Patent Publication Number 1,557,774 and Uhlin et al., 1979, Gene 6:91. At temperatures below 30° C., especially 25° C., the replicon maintains a relatively low copy number of about 10-15 copies per cell. When the temperature is raised to 37° C., copy control is lost and plasmid DNA containing the replicon amplifies to 1000-2000 copies per cell The particular runaway replicon exemplified herein is contained in the previously described plasmid pIM-I'-A3 starting material.

It is understood that the present invention is not limited to the use of any particular runaway replicon or copy number mutant. Other inducible runaway or high copy number replicons can be obtained by appropriate selection or can be constructed in accordance with the procedures disclosed in International Publication Number W082/02901 and Bittner and Vapnek. 1981, Gene 15:319. In addition, non-runaway replicons can also be used so long as they are functional in *E. coli* Bacillus, Streptomyces or other suitable microbial host cell. Examples of illustrative replicons include, but are not limited to, replicons from pMB1, ColE1, NR1, RK2, RK6, pSC101, RP1, RP4, F and the like, including bacteriophage that replicate in *E. coli;* replicons from pEL7, pEL103, SCP2, SCP2* and the like, including bacteriophage that replicate in Streptomyces; and replicons from pC194, pBS1, pE194, pUB110, pT127 and the like, including bacteriophage that replicate in Bacillus. Skilled artisans will appreciate that these and also a variety of runaway replicons can be substituted and used to construct expression vectors that are within the scope of the present invention. The expression vectors and method of this invention can be used in a wide range of host organisms, for example, gram-negative prokaryotic organisms such as *Escherichia coli*, for example, *E. coli* K12, *E. coli* K12 RV308, *E. coli* K12 HB101, *E. coli* K12 C600, *E. coli* K12 C600 $R_k^-M_k^-$, *E. coli* K12 RR1 and *E. coli* K12 MM294, Serratia, Pseudomonas, and the like gram-positive prokaryotic organisms such as Bacillus, for example, *B. subtilis*, *B. thuringiensis*, and *B. thuringiensis* var. israelensis, and Streptomyces, for example, *S. fradiae*, *S. ambofaciens*, *S. lividans* and *S. griseofuscus*. Although all of the embodiments of the present invention are useful, the vectors and transformants that comprise DNA encoding bovine growth hormone are preferred.

Preferred vectors include pCZ149, pCZ183, pCZ184, pCZ149.1 pCZ149.2. pCZ149.3, pCZ183.1, and pCZ183.2, and preferred transformants include *E. coli* K12 RV308/pCZ149, *E. coli* K12 RV308/pCZ183, *E. coli* K12 RV308/pCZ184, *E. coli* K12 RV308/pCZ149.1, *E. coli* K12 RV308/pCZ149.2, *E. coli* K12 RV308/pCZ149.3, *E. coli* K12 RV308/pCZ183 1, and *E. coli* K12 RV308/pCZ183.2.

Those skilled in the art will recognize that the expression vectors and method of this invention are used to transform suitable host organisms such that an exogenous protein product is expressed using standard fermentation conditions. The exogenous protein product is then isolated by routine methods from the resulting fermentation broth The following examples further illustrate the invention disclosed herein. Both an explanation of and the actual procedures for constructing the invention are described where appropriate.

EXAMPLE 1

Construction of Plasmid pNM789B

A. Construction of Plasmid pKEN021 and the XbaI-BamHI Fragment Thereof

The ~5.1 kb fragment produced by XbaI-BamHI cleavage of plasmid pKEN021 (106 in FIG. 3) was used as starting material. Plasmid pKEN021 is a derivative of pKEN111, (101 in FIG. 1 and further described in Lee, et al., 1981, J. Bact. 146: 861–866 and Zwiebel, et al., 1981, J. Bact. 145: 654–656), which is on deposit in *E. coli* CC620 (NRRL Deposit No. 15011) and which has a ~2.8kb fragment which contains the lipoprotein gene of *E. coli*. A description of this fragment is provided in Nakamura and Inouye, 1979, Cell 18: 1109–1117 In pKEN021, the 650 bp (base pair) sequence between the unique EcoRI and SalI restriction sites of pBR322 has been replaced by sequences taken from the lipoprotein gene of *E. coli*. The lipoprotein gene sequence (Nakamura and Inouye, 1979) includes a 462 bp AluI fragment, upstream from the first triplet (methionine) of the lipoprotein gene that contains the promoter, the 5' untranslated region and the ribosome binding site. A unique XbaI restriction site is located within the ribosome binding site 16 bp before the translation initiating methionine signal. A PvuII restriction site located 105 bp upstream from the translation termination codon of the structural gene was changed to a BamHI restriction site by the addition of a synthetic DNA linker (5'CCGGATCCGG3', obtained from Collaborative Research). The coding sequence for the last thirty-five amino acids of lipoprotein, the translation termination signal, and the sequence corresponding to the 3' untranslated region of the messenger RNA follow the BamHI site. Plasmid pKEN021 also includes some 850 bp of extraneous sequences unrelated to the lipoprotein gene and located downstream of it in the E. coli chromosome. These sequences were included as a consequence of the methods and restriction enzyme sites used in the original isolation of the gene.

Figure 2:
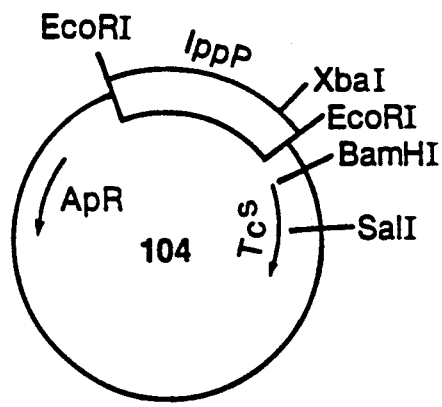
Figure 2:
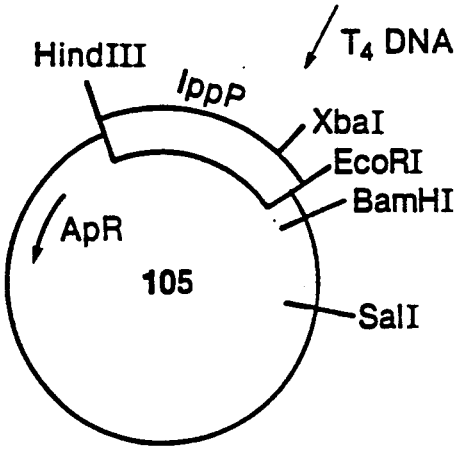
Figure 3:
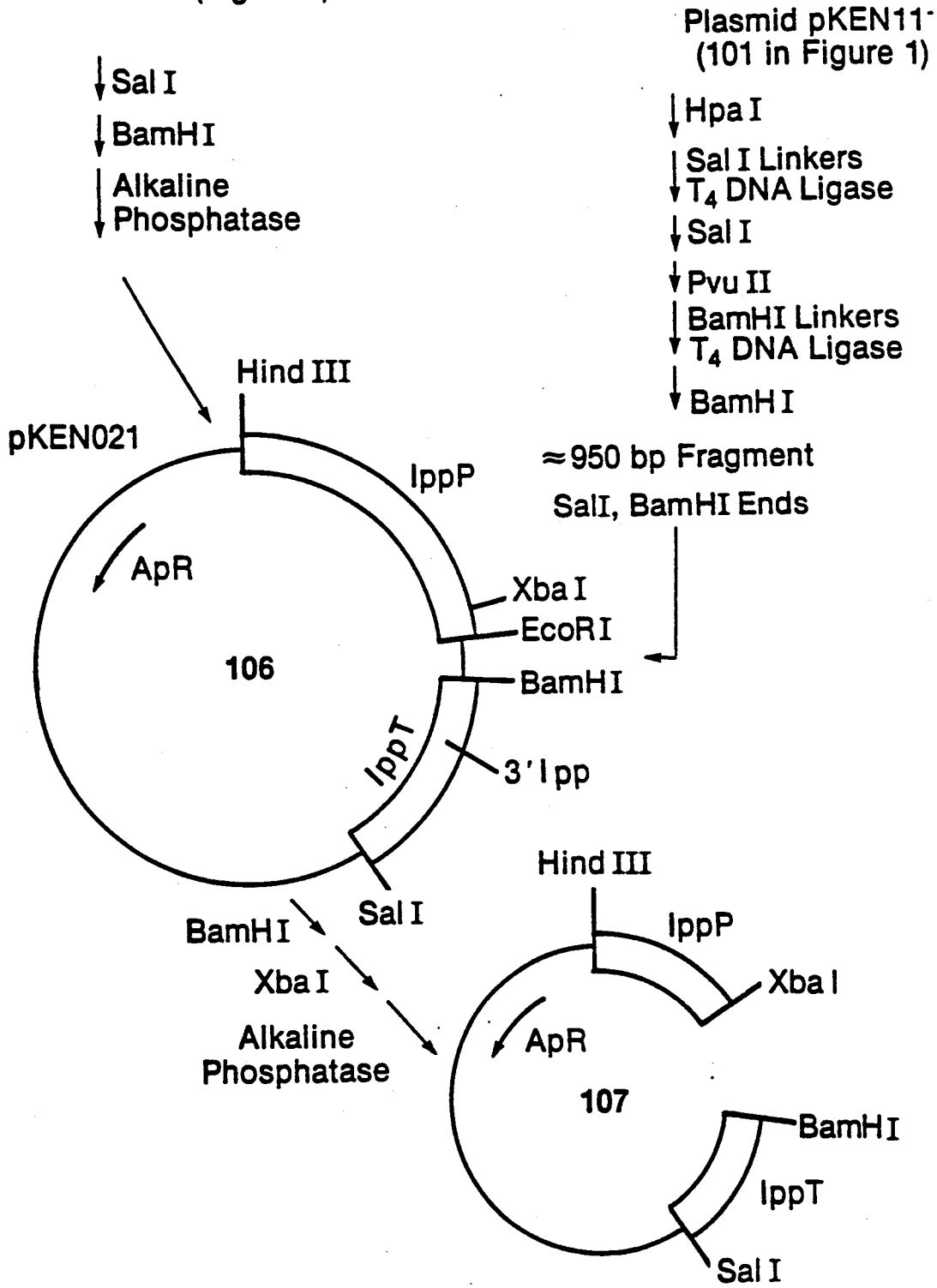
Figure 4:
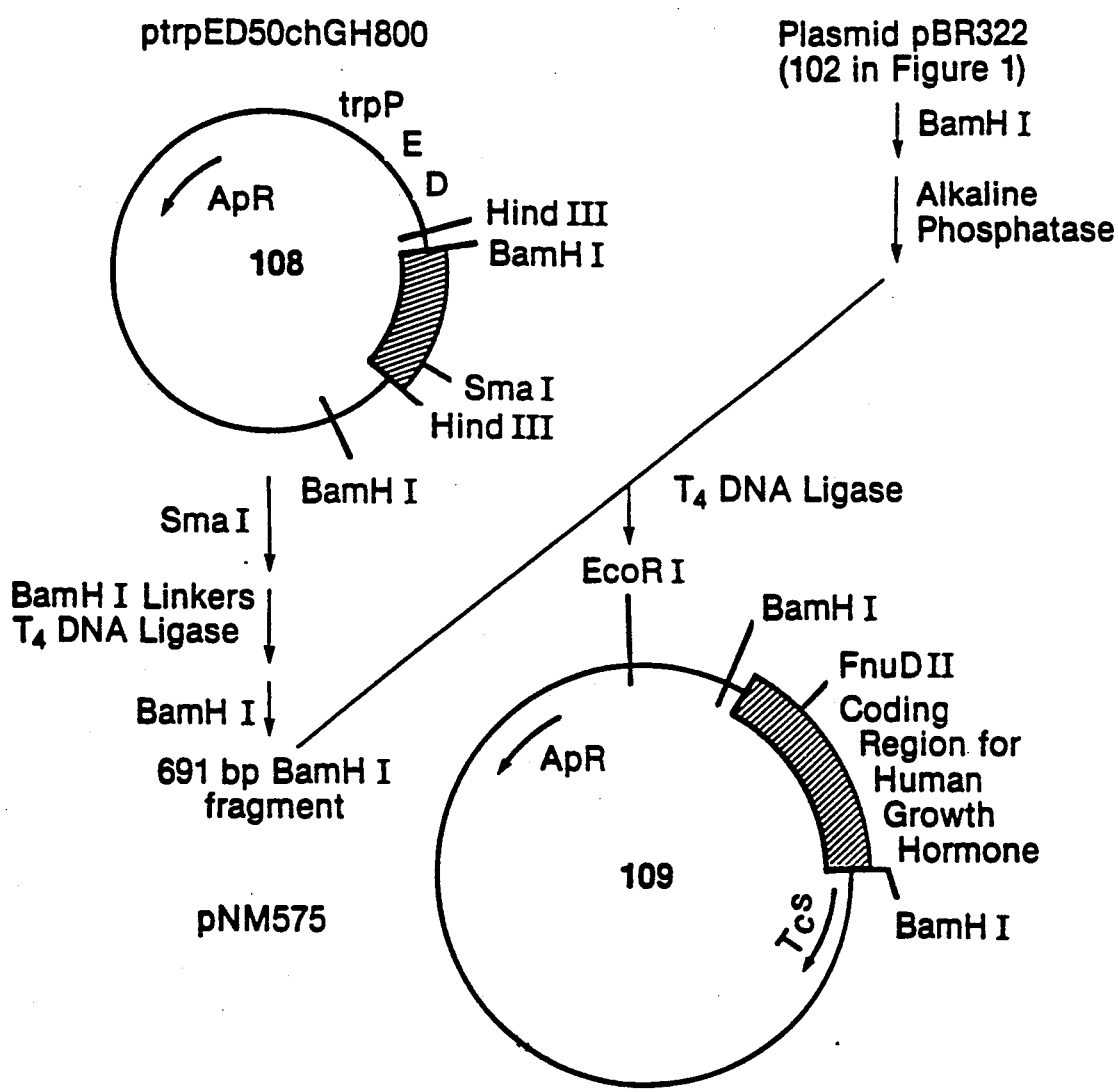
Figure 5:
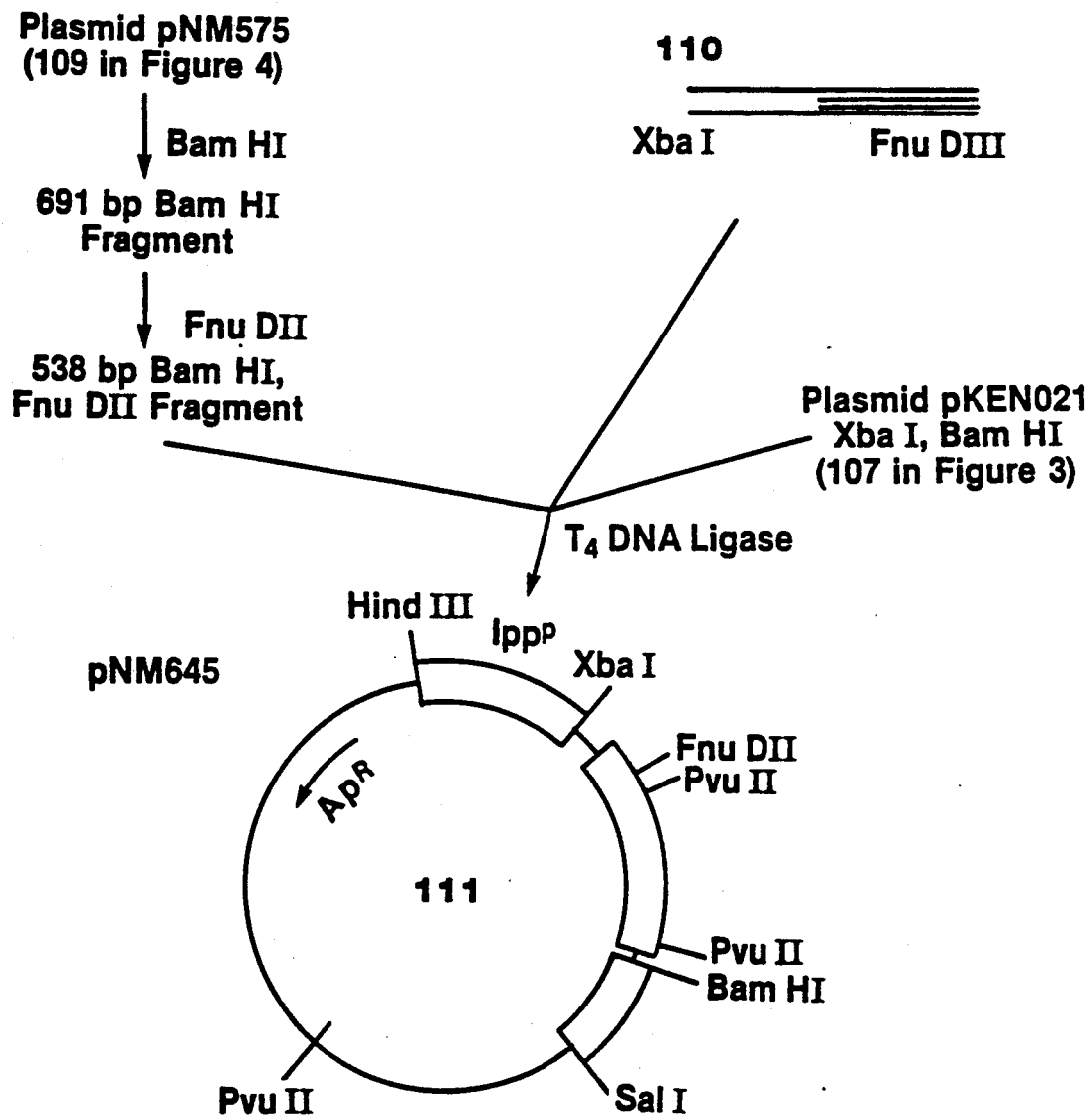
FIGS. 5-8—Schematic illustration of the construction protocol for plasmid pNM789B.
Figure 6:
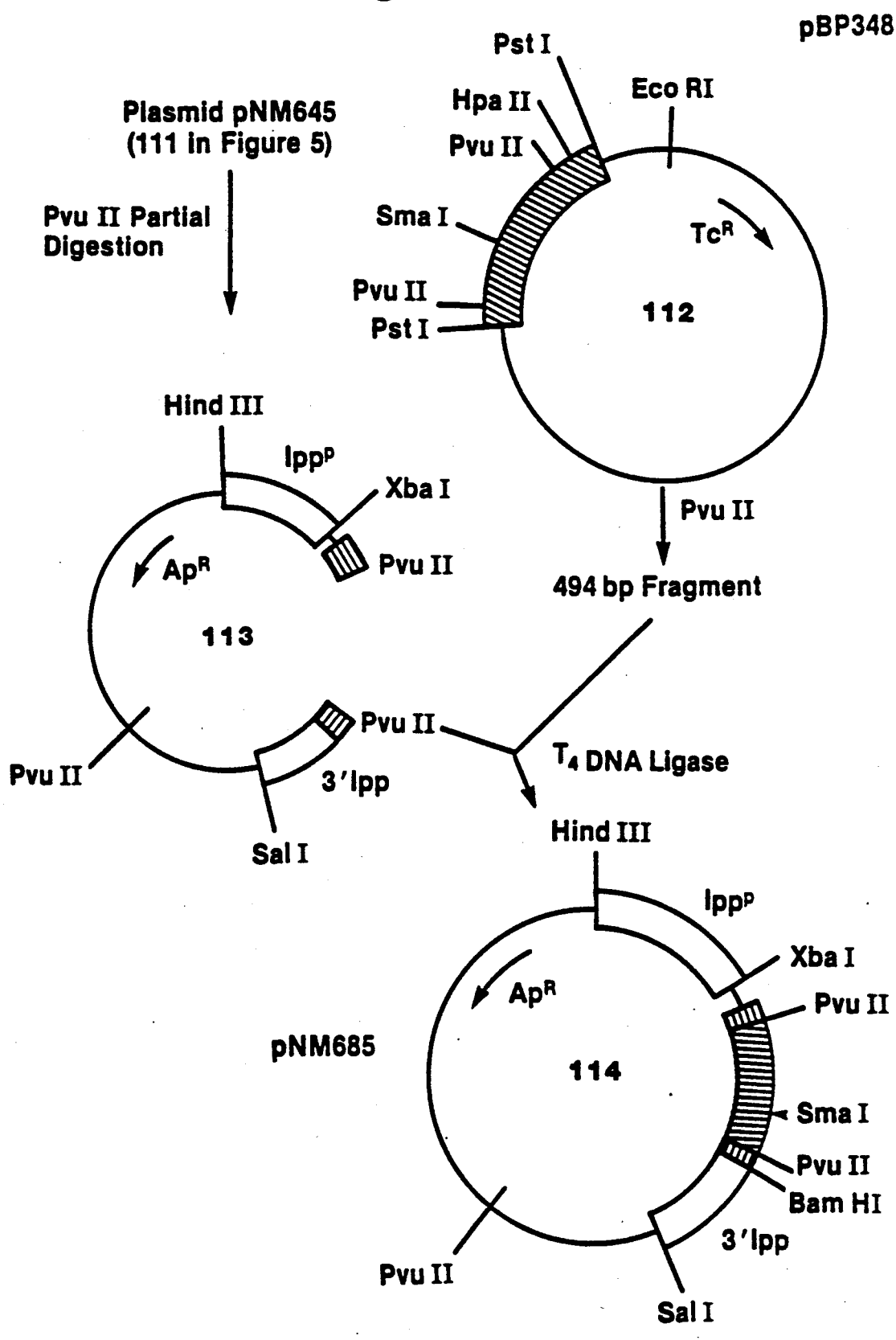
Figure 7:
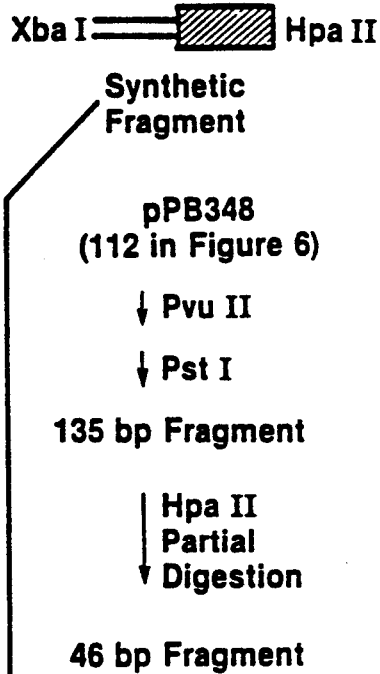
Figure 7:
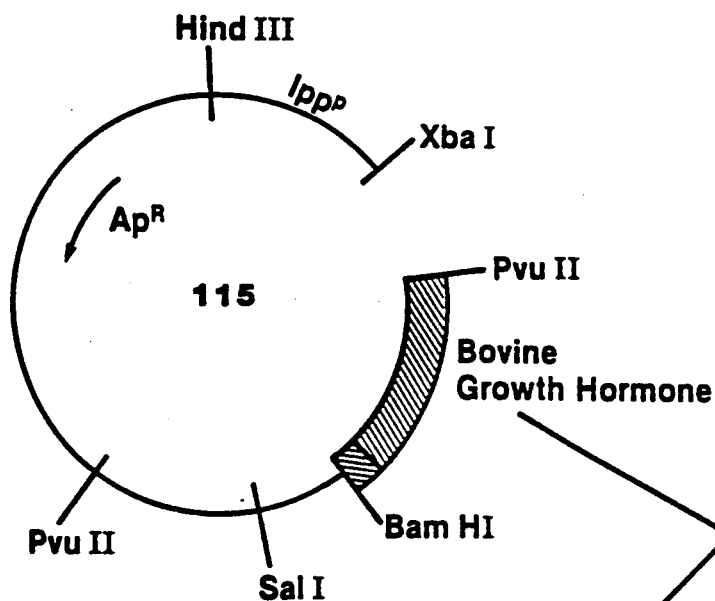
Figure 7:
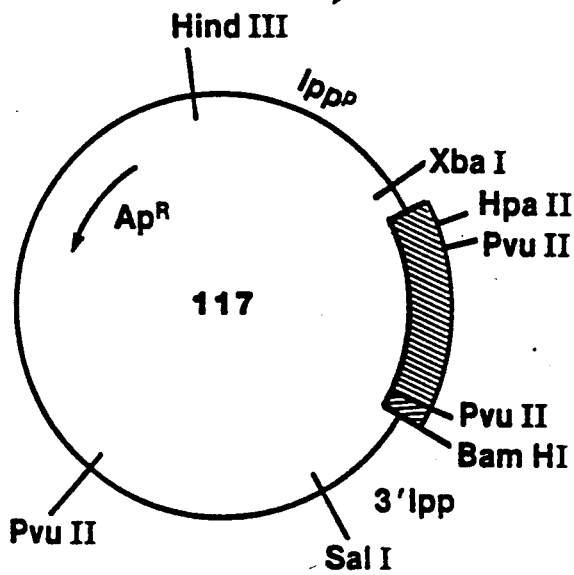
Figure 8:
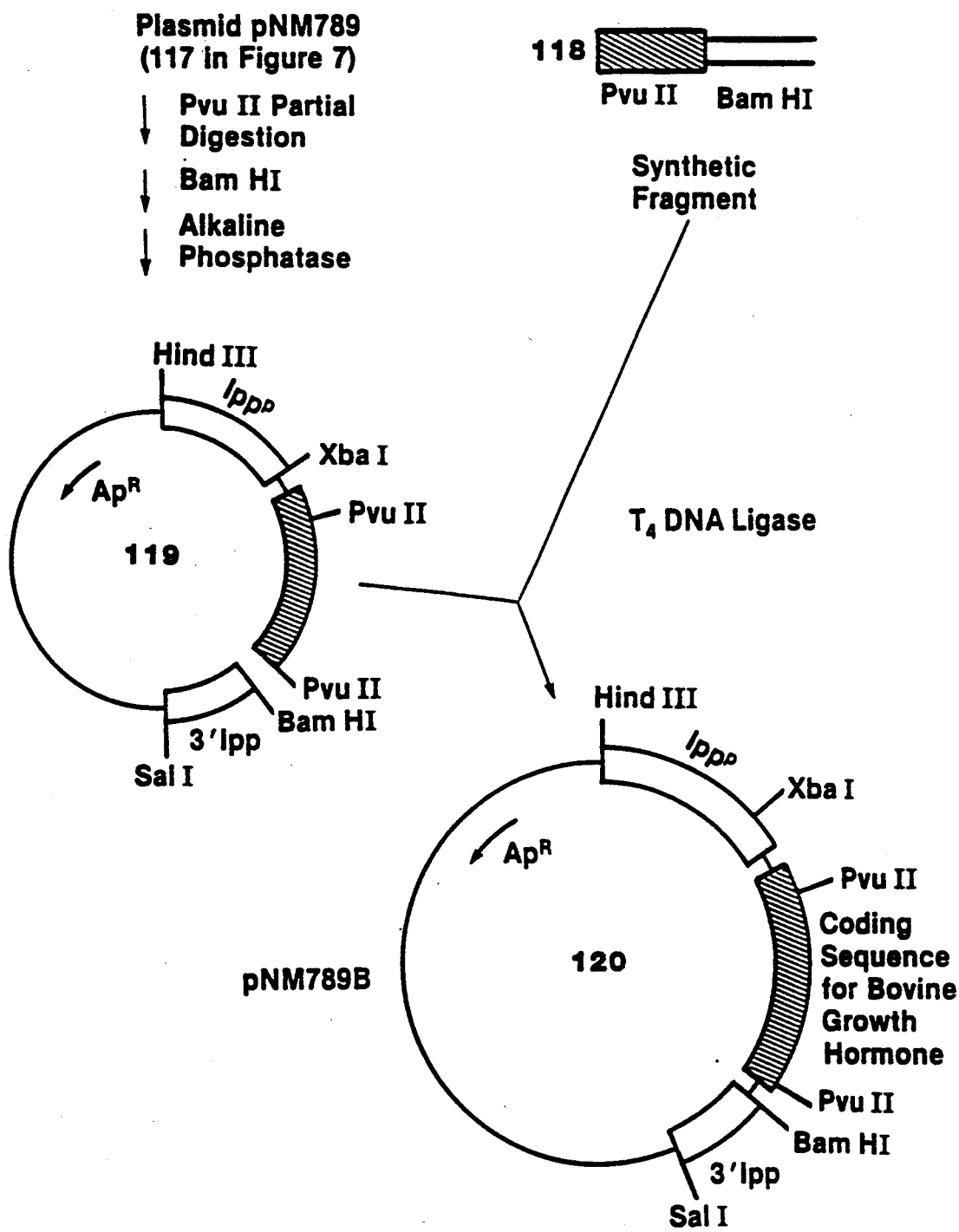

Referring to FIGS. 1, 2, and 3, plasmid pKEN021 is derived from pKEN111 in the following manner: About 50 μg of pKEN111 (101 in FIG. 1) are digested with 25 units of HpaII restriction enzyme in 300 μl of a buffer containing 20 mM Tris.HCl, pH 7.4, 10 mM MgCl$_2$, and 6 mM β-mercaptoethanol at 37° C. for 2 hours. The mixture is extracted twice with 300 μl of a 50:50 mixture of phenol and chloroform and the recovered aqueous phase is then precipitated with 2.5 volumes of ethanol and 0.1 volumes of 3M sodium acetate. The DNA pellet is dissolved in 100 μl of electrophoresis buffer and fractionated on a 5 percent polyacrylamide gel (acrylamide:bis ratio is 29:1 in all gels except where noted). The gel is stained in a solution containing 0.5 μg/ml of ethidium bromide and bands are visualized under long wave-length ultraviolet light. A 950 bp band is isolated and recovered from the gel by electroelution into a dialysis bag. After phenol/CHCl$_3$ extraction and ethanol precipitation, the recovered DNA (approximately 2.5 μg) is dissolved in 25 μl of TEN (10 mM NaCl, 10 mM Tris.HCl pH 7.4 and 1 mM sodium ethylenedinitrilotetraacetate (EDTA), pH 8.0).

About 2 μg of the 950 bp HpaII fragment are digested with AluI restriction enzyme in 200 μl of a buffer containing 50 mM NaCl, 6 mM Tris.HCl (pH 7.6), 6 mM MgCl$_2$, and 6 mM β-mercaptoethanol for 2 hours at 37° C. The DNA is fractionated on a 6 percent polyacrylamide gel and the 462 bp AluI fragment generated is recovered and purified by the method previously described The 462 bp AluI fragment (approximately 1 μg) is dissolved in 10 μl of T4 DNA ligase buffer (66 mM Tris.HCl pH 7.6, 10 mM MgCl$_2$, 10 mM dithiothreitol, 0.4 mM ATP) containing 150 picomoles of phosphorylated EcoRI linker (5'GGAATTCC3' from Collaborative Research) and 2 units T4 DNA ligase. After incubation at 4° C. for 16 hours, the mixture is heated at 65° C. for 10 minutes and diluted to 100 μl with the addition of EcoRI buffer (100 mM Tris.HCl pH 7.2, 50 mM NaCl 10 mM MgCl$_2$, 6 mM β-meroaptoethanol) and 40 units EcoRI enzyme. After 2 hours at 37° C., the sample is conventionally phenol/CHCl$_3$ extracted and ethanol precipitated. The DNA is then dissolved in 20 μl of T4 DNA ligase buffer containing 0.1 unit T4 DNA ligase and 0.1 μg pBR322 (102 in FIG. 1) which has been linearized with EcoRI and then treated with alkaline phosphatase. After ligation at 4° C. for 16 hours, the resultant DNA is used to conventionally transform E. coli strain K12 HB101. Transformants are selected on agar plates containing 12 μg/ml of tetracycline and plasmids isolated from resistant colonies by the rapid alkaline extraction procedure described in Birnboim and Doly, 1979, Nucleic Acids Research 7:1513–1523. A plasmid (103 in FIG. 1) containing a 399 bp XbaI-BamHI fragment (the desired orientation of the 470 bp EcoRI fragment is ascertained by the presence of the 399 bp XbaI-BamHI fragment) is selected and used as the starting material for the step next described.

About two μg of this plasmid (103 in FIG. 2) are digested with 2 units of HindIII enzyme in 50 μl HindIII buffer (60 mM NaCl, 10 mM Tris.HCl, pH 7.4, 10 mM MgCl$_2$ and 6 mM β-mercaptoethanol) for 1 hour at 37° C. After phenol/CHCl$_3$ extraction and ethanol precipitation, the DNA is dissolved in 200 μl of a buffer containing 300 mM NaCl, 30 mM sodium acetate pH 4.25, 1 mM ZnCl$_2$ and 200 units of S1 nuclease (Miles Laboratories). After 1 hour at 15° C., the reaction is stopped by phenol/CHCl$_3$ extraction and ethanol precipitation. The resultant DNA is dissolved in 10 μl T4 DNA ligase buffer containing 20 picomoles phosphorylated BamHI linkers (5'CCGGATCCGG3', from Collaborative Research) and 2 units T4 DNA ligase. After 16 hours at 4° C., the reaction mixture is heated at 65° C. for 10 minutes to inactivate the ligase and then diluted to 100 μl in BamHI buffer (150 mM NaCl, 20 mM Tris.HCl, pH 8.0, 10 mM MgCl$_2$, 6 mM β-mercaptoethanol) containing 20 units BamHI enzyme. After 2 hours at 37° C., the mixture is purified on a 1 percent agarose gel. The gel is stained and the larger fragment (~4.5 kb) is recovered by elution after freezing and then purified by phenol/CHCl$_3$ extraction and ethanol precipitation. The recovered fragment with BamHI cohesive ends is dissolved in 20 μl of T4 DNA ligase buffer containing 0.1 unit T4 DNA ligase. After 16 hours at 4° C., the DNA is used to transform E. coli HB101. Transformants are selected by resistance to ampicillin (Ap$^r$) at 100 μg/ml and screened for sensitivity to 10 μg/ml tetracycline (Tc$^s$). Several plasmids, prepared by the previously described Birnboim procedure from colonies which are Ap$^r$Tc$^s$, are examined for the absence of a HindIII site and the presence of a single BamHI site. EcoRI, SalI sequential digestion yields a 466 bp and a 305 bp fragment. A plasmid (104 in FIG. 2) with these characteristics is selected and then modified to convert the EcoRI site, located upstream of the lpp promoter, to a HindIII restriction site.

Two micrograms of plasmid (104 in FIG. 2) are digested in 100 μl of EcoRI buffer with 0.2 units of EcoRI for 10 minutes at 37° C. The reaction is stopped by heating for 10 minutes at 65° C. and then, after phenol/CHCl$_3$ extraction, the DNA is ethanol precipitated, dissolved in 200 μl of S1 nuclease buffer containing S1 nuclease at 1000 units/ml and reacted at 12° C. for 1 hour. The reaction is stopped by phenol/CHCl$_3$ extraction and ethanol precipitation. The resultant DNA is resuspended in 10 μl of T4 DNA ligase buffer containing 20 picomoles phosphorylated HindIII linker (5'CCAAGCTTGG3', from Collaborative Research) and 2 units of T4 DNA ligase After 16 hours at 4° C., the mixture is heated for 10 minutes at 65° C., diluted to 150 μl in HindIII buffer containing 10 units HindIII enzyme, incubated for 2 hours at 37° C. and then fractionated on a 1 percent agarose 9el. The largest band (equivalent to single cut plasmid) is conventionally recovered and purified, dissolved in 20 μl T4 ligase buffer containing 0.2 units T4 ligase, incubated 16 hours at 4° C. and then used to transform E. coli HB101. Transformants are selected for ampicillin resistance and plasmid isolates conventionally analyzed by restriction enzyme analysis. A plasmid (105 in FIG. 2) with an EcoRI-HindIII fragment of 474 bp is selected and used as the cloning vector for addition of the 3' region of the lpp gene.

About two μg of plasmid (105 in FIG. 3) are digested in 50 μl of SalI restriction buffer (150 mM NaCl, 6 mM Tris.HCl, pH 7.9, 6 mM MgCl$_2$, 6 mM β-mercaptoethanol) with 2 units of SalI for 1 hour at 37° C. and then diluted to 150 μl in BamHI buffer containing 2 units BamHI. After 1 hour at 37° C, 2.5 units of alkaline phosphatase are added and then incubation is continued for 1 hour at 65° C. The material is phenol/CHCl$_3$ extracted, ethanol precipitated, dissolved in TEN, and used as a cloning vector for the lpp 3' fragment.

To obtain the fragment containing the lpp 3' region, 10 μg of pKEN111 (101 in FIG. 3) are digested in 200 μl of HaiI buffer (20 mM KCl, 10 mM Tris.HCl, pH 7.4, 10 mM MgCl$_2$ and 6 mM β-mercaptoethanol) with 10 units of HaiI for 2 hours at 37° C. After phenol/CHCl$_3$ extraction and ethanol precipitation, the DNA is dissolved in 10 μl T4 DNA ligase buffer containing 20 picamoles phosphorylated SalI linker (5'GGTCGACC3', from Collaborative Research) and 2 units T4 DNA ligase and then incubated for 16 hours at 4° C. The ligase is inactivated by heating at 65° C. for 10 minutes. The resultant material is diluted to 100 μl in SalI buffer containing 10 units of SalI and incubated 1 hour at 37° C., and then diluted to 300 μl in PvuII buffer (60 mM NaCl, 6 mM Tris.HCl, pH 7.5, 6 mM MgCl$_2$, 6 mM β-mercaptoethanol) containing 10 units PvuII restriction enzyme. After 1 hour at 37° C., the DNA is fractionated on a 5 percent polyacrylamide gel. Approximately 0.5 μg of a 950 bp fragment is recovered, purified and dissolved in TEN. Two-tenths microgram of the fragment is diluted into 20 μl T4 DNA ligase buffer containing 20 picomoles phosphorylated BamHI linker (5'CCGGATCCGG3', from Collaborative Research) and 2 units T4 DNA ligase and then incubated for 16 hours at 4° C. The resultant DNA is then heated for 10 minutes at 65° C., diluted to 100 μl in BamHI buffer containing 20 units BamHI, incubated at 37° C. for 2 hours and then fractionated on a 5 percent polyacrylamide gel to remove excess linker molecules. The resultant 950 bp fragment having BamHI and SalI cohesive ends is conventionally purified and dissolved in 20 μl of T4 DNA ligase buffer containing both 0.2 μg of the cloning vector described previously and 0.2 units T4 DNA ligase. After incubation for 16 hours at 4° C., the DNA is used to transform E. coli K12 HB101. Plasmids are prepared from ampicillin resistant transformants and conventionally analyzed for the SalI-BamHI fragment. The desired plasmid (~5.2 kb) is designated pKEN021 (106 in FIG. 3).

Ten micrograms of pKEN021 were digested at 37° C. in 200 μl of XbaI/BamHI buffer (150 mM NaCl, 10 mM Tris.HCl, pH 8, 10 mM MgCl$_2$, 6 mM β-mercaptoethanol) using 10 units of BamHI for 1 hour followed by 10 units of XbaI for an additional hour at 37° C. The desired XbaI-BamHI-digested DNA was then treated with 2.5 units of alkaline phosphatase for 1.5 hours at 65° C., phenol/CHCl$_3$ extracted, collected by ethanol precipitation, and dissolved in 50 μl of TEN for future use (107 in FIG. 3).

B. Construction of Plasmid pNM575

Plasmid ptrpED50chGH800 (108 in FIG. 4), described in Martial et al., 1979, Science 205:602–607 was used as the source of a DNA fragment containing the coding sequence for a portion of the human growth hormone gene. This fragment can also be constructed synthetically (Itakura et al., 1977 and Crea et al., 1978) or can be obtained using recognized methodology described by Goodman et al., 1979, Methods in Enzymology 68:75–90, by isolating mRNA coding for human growth hormone from human pituitaries. The human growth hormone gene portion of plasmid ptrpED50chGH800 contains a unique SmaI restriction site 6 bp downstream from the translation termination codon of the gene. This site was changed to a BamHI site using the following procedure: 6 μg of the plasmid were digested with 6 units of SmaI in 200 μl of SmaI restriction buffer (15 mM Tris.HCl, pH 8.0, 6 mM MgCl$_2$, 15 mM KCl and 6 mM β-mercaptoethanol) for 1.5 hours at 37° C. After digestion was complete, phenol/CHCl$_3$ extraction was performed and the DNA was recovered by ethanol precipitation and then dissolved in 24 μl of TEN. Forty picomoles of phosphorylated BamHI adapter fragment (Collaborative Research) were added to 0.5 μg (0.2 picomole ends) of the above-digested plasmid in 16 μl of ligase buffer containing 2 units T4 DNA ligase. The mixture was incubated 2 hours at 22° C., 16 hours at 4° C. and then 10 minutes at 65° C. BamHI cohesive termini were generated by conventional digestion with BamHI restriction enzyme. The enzyme cleaved the linker sequence as well as the BamHI site located at the beginning of the cloned human growth hormone cDNA sequence. This yielded a 691 bp fragment with cohesive BamHI ends which was separated on a 6 percent polyacrylamide 9el and then conventionally recovered. The recovered DNA fragment was ligated (using 0.2 unit T4 DNA ligase in 20 μl of buffer under previously described conditions) with 0.2 μg of BamHI-digested and alkaline phosphatase-treated pBR322 (102 in FIG. 4). After 16 hours at 4° C., the material was used to transform E. coli strain JA221 (NRRL No. B-15014) in substantial accordance with the transformation procedure of Wensink et al., 1974, Cell 3:315–325. Transformants were selected on agar plates containing 100 μg/ml ampicillin and then plasmids were conventionally isolated and identified by restriction enzyme and gel electrophoretic analysis. Desired plasmids, designated as pNM575 (109 in FIG. 4), contain a BamHI fragment of approximately 700 bp and were conventionally amplified for future use.

Construction of Plasmid pNM645

The DNA sequence of mature human growth hormone contains one FnuDII site which is 47 bp from the first nucleotide. Twenty-five micrograms of pNM575 were digested in 250 μl of BamHI buffer with 25 units of BamHI at 37° C. for 1 hour. The 691 bp fragment with BamHI cohesive termini was conventionally isolated from a 6 percent polyacrylamide gel and purified. After purification of the fragment, one third of it (equivalent to 8 μg of plasmid) was digested in 100 μl of FnuDII buffer (6 mM NaCl, 6 mM Tris.HCl, pH 7.4, 6 mM MgCl$_2$, 6 mM β-mercaptoethanol) with 2.5 units FnuDII for 1.5 hours at 37° C. Electrophoresis on a 6 percent polyacrylamide gel and standard recovery procedures were used to isolate a 538 bp DNA fragment containing the coding sequence for the last 175 amino acids of the gene followed by a translation stop signal.

A double stranded DNA fragment (110 in FIG. 5) was synthesized by the phosphotriester method to join the lpp promoter region with the human growth hormone coding region. The double stranded DNA fragment (110 in FIG. 5) has the following sequence:

The fragment was prepared by recognized phosphotriester methodology by which the following segments were prepared
1) CTAGAGGGTAT
2) TAATAATG
3) CATTGGATGAT
4) GATGATAAG
5) CAACCATTCCC
6) TTATCCAGGC
7) TTTTTGACAACG
8) CTATGCTCCG
9) CATTATTAATACCCT
10) ATGGGAA
11) CTTATCATCATCCA
12) GGTTGGGAA
13) GGATAAGGGAAT
14) GTCAAAAAGCCT
15) CGGAGCATAGCGTT Using the above-prepared segments, the T4 ligase catalyzed joining reactions were performed stepwise as described below:

a) 5'-Unphosphorylated segment 1 was joined to 5'-phosphorylated segment 2 in the presence of 5'-phosphorylated segment 9 using T4 ligase to form DNA duplex 1 (Brown et al., 1979, Methods in Enzymology 68:109–151). The duplex was isolated by preparative gel electrophoresis on 15% polyacrylamide.

b) 5'-Phosphorylated segment 3 was joined to 5'-phosphorylated segment 4 in the presence of 5'-phosphorylated segment 11 using T4 ligase to form DNA duplex 2 which was purified by 15% polyacrylamide gel electrophoresis.

c) 5'-Phosphorylated segment 5 was joined to 5'-phosphorylated segment 6 in the presence of 5'-phosphorylated segments 12 and 13 using T4 ligase to form DNA duplex 3 which was purified by 15% polyacrylamide gel electrophoresis.

d) 5'-Phosphorylated segment 7 was joined to 5'-phosphorylated segment 8 in the presence of 5'-phosphorylated segment 1% and 5'-unphosphorylated segment 15 using T4 ligase to form DNA duplex 4 which was purified by 15% polyacryl-amide gel electrophoresis.

e) The DNA duplexes 2, 3 and 4 then were joined together by T4 ligase to form DNA duplex 5 which was purified by 15% polyacrylamide gel electrophoresis.

f) 5'-phosphorylated segment 10 and DNA duplex 5 were added, in the presence of T4 ligase, to the DNA duplex 1. The resulting DNA duplex (110 in FIG. 5) was purified by 10% polyacrylamide gel electrophoresis. This DNA duplex then was enzymatically phosphorylated using T4 polynucleotide kinase and [γ-$p^{32}$]ATP by following established procedure.

The expression plasmid pNM645 was constructed by enzymatically joining 0.1 picomole (0.4 μg) of the XbaI-BamHI fragment of plasmid pKEN021 (107 in FIG. 5), 0.025 picomoles synthetic DNA fragment (110 in FIG. 5) and 0.3 picomoles (0.08 μg) of 538 bp fragment (from 109 in FIG. 5) in 24 μl of ligation buffer using 1.5 units T4 DNA ligase. After incubation for 16 hours at 4° C, the mixture was used to transform E. coli JA221 as previously described. Transformants were selected on agar plates containing 100 μg/ml ampicillin and were conventionally cultured as a preferred source of the desired expression plasmid.

Expression of human growth hormone was detected by a standard radioimmunoassay procedure (Twomey et al., 1974, Clin. Chem. 20:389–391) and was determined to be at least 2 million molecules per cell.

D. Construction of Plasmid pNM789

Plasmid pNM645 (111 in FIG. 6), the expression plasmid for human growth hormone, was used as the starting material for construction of a plasmid expressing Met-Phe-Pro-Leu-Asp-Asp-Asp-Asp-Lys-bGH.

Plasmid pBP348 (112 in FIG. 6), described in Miller et al., 1980, J. Biol. Chem. 255:7521–7524, was used as the source of two DNA fragments containing the coding sequence for a portion of the bovine growth hormone gene. The plasmid contains an 831 bp bovine growth hormone-encoding sequence cloned in the PstI restriction site of pBR322. As an alternative to the method described in Miller et al., 1980, the sequence for bovine growth hormone can be constructed synthetically (Itakura et al., 1977 and Crea et al., 1978) or can also be obtained from messenger RNA isolated from bovine pituitaries by the now routine procedures described by Goodman et al., 1979.

The coding sequences for human growth hormone and bovine growth hormone are very similar and show much homology. Particularly useful in the construction of the expression plasmid for bovine growth hormone were the fragments generated by digestion with the restriction enzyme PvuII. The size of the fragments produced are 497 bp in human growth hormone and 494 bp in bovine growth hormone and the corresponding restriction sites occur in the same reading frames in both sequences.

Ten micrograms of pNM645 (111 in FIG. 6) were partially digested with 1 unit of PvuII in 200 μl of PvuII restriction buffer (60 mM NaCl, 6 mM Tris.HCl, pH 7.5, 6 mM MgCl$_2$, 6 mM β-mercaptoethanol) for 10 minutes at 37° C. After the reaction was stopped by heating at 65° C. for 10 minutes, the DNA was treated with alkaline phosphatase and the fragments separated on a one percent agarose gel. The linear DNA fragment (113 in FIG. 6) of the size that corresponded to DNA with the 497 bp PvuII fragment missing (runs slightly faster than single cut plasmid) was conventionally excised, purified and used in the construction of an intermediate plasmid (114 in FIG. 6).

A 494 bp PvuII fragment of plasmid pBP348 was prepared by digesting 10 μg of the plasmid in 200 μl PvuII buffer containing 10 units of PvuII for 1 hour at 37° C. The fragments were separated on a 6 percent polyacrylamide gel and the desired 494 bp fragment (from 112 in FIG. 6) was conventionally visualized and purified.

Intermediate plasmid (114 in FIG. 6) was constructed by reacting 0.2 μg of the plasmid pNM645 PvuII fragment with 0.05 μg of 494 bp fragment in 20 μl of T4 DNA ligase buffer containing 2 units T4 DNA ligase for 16 hours at 4° C. After transformation and selection of transformants for ampicillin resistance, the plasmids were conventionally analyzed for the presence and proper orientation of the 494 bp PvuII fragment Plasmids with a 494 bp PvuII fragment and a 440 bp XbaI-SmaI fragment are selected for use in further constructions.

Ten micrograms of the intermediate plasmid (114 in FIG. 7) were digested with 1 unit PvuII in 200 μl PvuII buffer for 5 minutes at 37° C. After the heating at 65° C. for 10 minutes, the mixture was spread on a 1 percent agarose gel and linear DNA having only a single PvuII cut per molecule was recovered and purified. This recovered material (approximately 3 μg) was digested completely with 5 units of XbaI and treated with alkaline phosphatase. The fragments were spread on a 1 percent agarose gel and the largest fragment (missing the 109 bp fragment between the XbaI and the first PvuII site in human and bovine growth hormone) was conventionally recovered (115 in FIG. 7).

The DNA sequence for the first 23 amino acids (69 bp) of bovine growth hormone to the first PvuII site contains 2 HpaII restriction sites, the first of which is 23 bp from the first nucleotide of the coding sequence. A 63 bp fragment (116 in FIG. 7) was synthesized by the phosphotriester method. This fragment corresponds to the 19 bp sequence from the XbaI site in the lpp ribosome binding site through the ATG translational start signal followed by the coding sequence for Phe-Pro-Leu-Asp-Asp-Asp-Asp-Lys (24 bp) and 20 nucleotides of the coding sequence of bovine growth hormone (from Phe to the first HpaII site). The fragment has the following sequence:

b) 5'-Phosphorylated segments 3, 4 and 5 were joined in the presence of 5'-phosphorylated segments 7 and 8 and 5'-unphosphorylated segment 9 using T4 ligase to form DNA duplex 2 which was purified by 15% polyacrylamide gel electrophoresis.

c) Duplexes 1 and 2 then were joined by T4 ligase to form DNA duplex (116 in FIG. 7) which was purified by 15% polyacrylamide gel electrophoresis. This DNA duplex then was enzymatically phosphorylated using T4 polynucleotide kinase and [γ-p$^{32}$] ATP following established procedure.

The DNA fragment of 46 bp which runs from the above-described HpaII site to the PvuII site can either be constructed synthetically or obtained from the original pBP348 plasmid. Accordingly, one hundred micrograms of plasmid pBP348 were digested in 400 μl of PvuII buffer with 50 units of PvuII for 2 hours at 37° C. After phenol extraction and ethanol precipitation, the DNA was dissolved in 400 μl of PstI buffer (50 mM NaCl, 6 mM Tris.HCl, pH 7.4, 6 mM MgCl$_2$, 6 mM β-mercaptoethanol) with 50 units of PstI for 2 hours at 37° C. The DNA fragments were spread on a 6 percent polyacrylamide gel and the 135 bp fragment containing the desired 46 bp sequence was recovered and purified by standard procedures. One-third of the recovered DNA (equivalent to 33 μg) was subjected to limited digestion by 1 unit of HpaII restriction enzyme in 100 μl HpaII buffer (20 mM Tris.HCl, pH 7.4, 7 mM MgCl$_2$, 6 mM β-mercaptoethanol) for 40 minutes at 37° C. After heating at 65° C. for 10 minutes, the DNA fragments were run on a 5 percent acrylamide gel (acrylamide:bis ratio 19:1) along with an appropriate size marker. The desired 46 bp fragment yielded by HpaII partial digestion of the 135 bp fragment (from 112 in FIG. 7) was purified by standard procedures.

Two-tenths microgram of the XbaI-PvuII fragment of plasmid vector (115 in FIG. 7), 3.2 picomoles of synthetic 63 bp fragment (116 in FIG. 7) and 0.5 picomoles 46 bp fragment (from 112 in FIG. 7) were incubated in 10 μl ligation buffer with 2 units of T4 DNA

```
XbaI
5'-CTAGAGG GTA TTA ATA ATG TTC CCA TTG GAT GAT GAT GAT AAG-
    ||| ||| ||| ||| ||| ||| ||| ||| ||| ||| ||| ||| |||
3'-     TCC CAT AAT TAT TAC AAG GGT AAC CTA CTA CTA CTA TTC-

TTC CCA GCC ATG TCC TTG TC  -3'   HpaII
||| ||| ||| ||| ||| ||| ||
AAG GGT CGG TAC AGG AAC AGGC-5'
```

In producing the 63 bp fragment, the following nine segments were prepared:
1) CTAGAGGGTAT
2) TAATAATGTTCC
3) CATTGGATGAT
4) GATGATAAGTTCC
5) CAGCCATGTCCTTGTC
6) ATGGGAACATTATTAATACCCT
7) TTATCATCATCATCCA
8) ATGGCTGGGAAC
9) CGGACAAGGAC Using the above-prepared segments, the T4 ligase catalyzed joining reactions were performed stepwise as described below:

a) 5'-Unphosphorylated segment 1 was joined to 5'-phosphorylated segment 2 in the presence of 5'-phosphorylated phosphorylated segment 6 using T4 ligase to form DNA duplex 1 which was purified by 15% polyacrylamide gel electrophoresis.

ligase for 16 hours at 4° C. The ligation mixture was used to transform E. coli JA221 and the resultant transformants, which thus contained the desired plasmid pNM789, were selected by ampicillin resistance. The identity of plasmid pNM789 (117 in FIG. 7) was confirmed by conventionally screening for the presence of both the 494 bp PvuII the 109 bp XbaI-PvuII fragments.

E. Final Construction of Plasmid pNM789B

Plasmid pNM789 (117 in FIG. 8) requires one amino acid codon change for complete conversion to bovine growth hormone. This was accomplished by the removal of the 28 bp PvuII to BamHI fragment of pNM789 and replacement with a synthetic double stranded fragment having the following sequence (118 in FIG. 8):

Ten micrograms of pNM789 were digested with 1 unit of PvuII in 200 μl PvuII buffer for 5 minutes at 37° C. After heating 10 minutes at 65° C., the mixture was diluted to 300 μl with the addition of BamHI buffer, digested to completion with 10 units of BamHI for 1 hour at 37° C., treated with 5 units of alkaline phosphatase and incubated for 1 hour at 65° C. The DNA fragments were separated on a 1 percent agarose gel and a DNA fragment (119 in FIG. 8) the size of single cut plasmid pNM789 was conventionally purified. Two-tenths microgram of this fragment was ligated with 5 picomoles of synthetic fragment using 2 units of T4 ligase in 20 μl ligase buffer. The ligation was carried out overnight at 4° C. Following transformation, several plasmids were isolated and screened for the appropriate PvuII (494bp) and XbaI-BamHI (628bp) fragments. Plasmids comprising the aforementioned fragments constituted the desired plasmid pNM789B (120 in FIG. 8).

EXAMPLE 2

Construction of Plasmid pCZ101 and *E. coli* K12 RV308/-pCZ101

A. Isolation of Plasmid pIM-I'-A3

The bacterium *E. coli* K12/pIM-I'-A3 (NRRL B-15733) was cultured in TY broth (1% tryptone, 0.5% yeast extract, 0.5% sodium chloride, pH 7.4) with 50 μg/ml of kanamycin at 25° C. according to conventional microbiological procedures After the culture was diluted 1:10 into fresh broth and after 3 hours incubation at 37° C., about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet was resuspended in about 100 μl of freshly prepared lysozyme solution (2 μg/ml) which contained 2 μg/ml lysozyme, 50 mM glucose, 10 mM EDTA (diaminetetracetate) and 25 mM Tris.HCl, pH 8. About 200 μl. of alkaline SDS (sodium dodecyl sulfate) solution (0.2N NaOH, 1% SDS) were added and the tube was gently inverted and then kept at 0° C. until lysis was complete (~5 minutes). Next, about 150 μl of 3M sodium acetate were added and the contents of the tube mixed gently by inversion for a few seconds.

The tube was maintained at 0° C. for at least 60 minutes and then centrifuged for 15 minutes to yield an almost clear supernatant. The supernatant was transferred to a second centrifuge tube to which 3 volumes of cold 100% ethanol were added. After the tube was held on dry ice ethanol for 5 minutes, the resultant precipitate was collected by centrifugation (5 minutes) and the supernatant was removed by aspiration. The collected pellet was dissolved in 100 μl of TE (10 mM Tris.HCl, pH 8.0, 1 mM EDTA) and constituted the desired pIM-1'-A3 plasmid DNA.

B. XbaI-BamHI Digestion of Plasmid pNM789B and generation of the ~0.6 kb XbaI-BamHI Fragment About 5 μg of plasmid pNM789B DNA in 50 μl Hi Salt buffer* were incubated with 10 units each of BamHI and XbaI restriction enzymes at 37° C. for about 1 hour. After the addition of 5 μl of 3M sodium acetate pH 7.0, the DNA was precipitated with 3 volumes of 100% ethanol. The desired DNA digest was dissolved in 100 μl of TE buffer and stored at 0° C. for future use.

*Hi Salt buffer was conventionally prepared with the following composition:
100 mM NaCl
20 mM Tris.HCl, pH8.0
10 mM MgCl₂
5 mM β-mercaptoethanol

C. XbaI-BamHI Digestion of Plasmid pIM-I'-A3

The desired digestion was carried out in substantial accordance with the procedure of Example 2B except that plasmid pIM-I'-A3 rather than plasmid pNM789B was used. The desired DNA was dissolved in about 100 μl of TE buffer and stored at 0° C. for future use.

D Ligation and Transformation

About 1 μg of the plasmid pIM-1'-A3 digest, 1 μg of the plasmid pNM789B XbaI-BamHI digest, 40 μl water, 5 μl (5 mM) ATP, 5 μl ligation mix* and 5 units T4 DNA ligase were incubated at 20° C. for about 2 hours. After incubation at 65° C. for 2 minutes followed by cooling on ice, the resultant ligation mixture was used to transform, in substantial accordance with the transformation procedure of Wensink, 1974, Cell 3:315, *E. coli* K12 RV308 on TY plates (1% tryptone, 0.5% yeast extract, 0.5% sodium chloride, 1.5% agar, pH 7.4) containing 50 μg/ml of kanamycin. Bacterial strain *E. coli* K12 RV308 has been deposited and made part of the permanent stock culture collection of the Northern Regional Research Laboratory, Peoria, Ill., from which it is available to the public under the accession number NRRL B-15624.

*Ligation mix (buffer) can be prepared with the following composition:
500 mM Tris.HCl, pH 7.8
200 mM Dithiothreitol
100 mM MgCl₂

Figure 9:
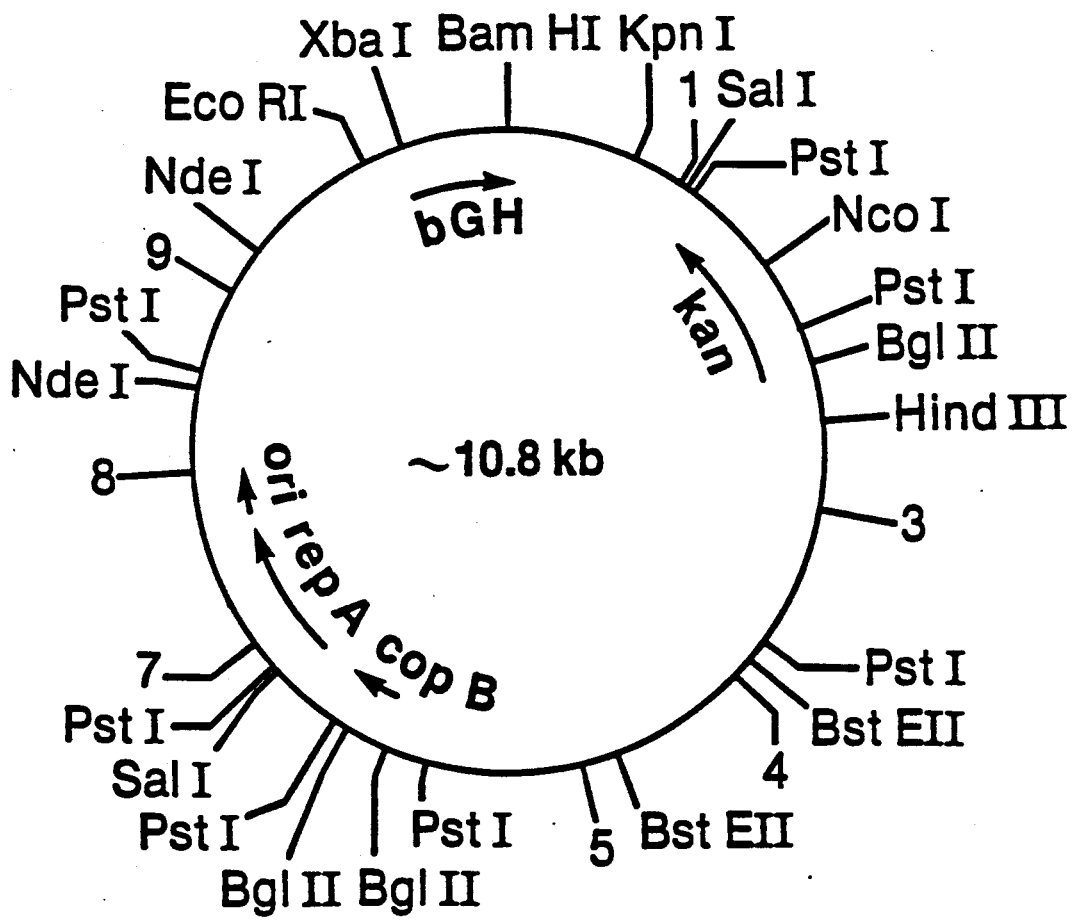
FIG. 9—Restriction site map of plasmid pCZ101.

Some of the resultant transformants, as conventionally shown by agarose gel electrophoresis (Maniatis et al., 1982) and other tests, contained only the desired ~10.8 kb plasmid (FIG. 9). Such a transformant, herein designated as *E. coli* K12 RV308/pCZ101, was selected, plated on TY agar containing appropriate antibiotics and then cultured using conventional microbiological techniques. The resultant cells were used to isolate plasmid pCZ101 in substantial accordance with the procedure of Example 1A.

EXAMPLE 3

Construction of Plasmid pCZ118 and *E. coli* K12 RV308/pCZ118

A Construction of the 9.2 kb EcoRI-NdeI Fragment of Plasmid pCZ101

Plasmid pCZ101 DNA was obtained in substantial accordance with the teaching of Example 2A, except that *E. coli* K12 RV308/pCZ101 rather than *E. coli* K12 pIM-1'-A3 was used. The desired fragment was constructed in substantial accordance with the teaching of Example 2B, except that plasmid pCZ101 and the EcoRI and NdeI restriction enzymes were used rather than plasmid pNM789B and the BamHI and XbaI restriction enzymes, respectively. The desired 9.2 kb EcoRI-NdeI restriction fragments were conventionally separated and isolated by agarose gel electrophoresis (Maniatis et al., 1982) and then dissolved in about 100 μl of TE buffer and stored at 0° C. for future use.

A. Ligation and Transformation

About 1 μg of the plasmid pCZ101 ~9.2 kb EcoRI-NdeI fragment was incubated with the Klenow Polymerase I and the four deoxyribonucleotides to fill in the single strand portions. Klenow Polymerase I (commercially available from Boehringer-Mannheim Biochemicals, 7941 Castleway Drive, P.O. Box 50816, Indianapolis, Ind. 46250) is the fragment obtained by proteolytic cleavage of DNA Polymerase I. It contains the 5' → 3' polymerizing activity, the 3' → 5' exonucleolytic activity, but not the 5' →3' exonucleolytic activity of the parental enzyme (Kornberg, 1974, W. H. Freeman and Co., SFO, 98).

The reaction mixture was thus heated to 50° C. and let cool slowly to 10° C., whereafter 4 μl of Klenow enzyme were added. After 15 minutes incubation at room temperature, followed by 30 minutes incubation at 37° C., the reaction was stopped by the addition of 5 μl of 0.25 molar EDTA. The reaction mixture was phenol extracted, chloroform extracted, and ethanol precipitated. The DNA was resuspended in ligation buffer, ligated, and the resultant plasmid used to transform *E. coli* K12 RV308 in substantial accordance with the teaching of Example 2D.

Figure 10:
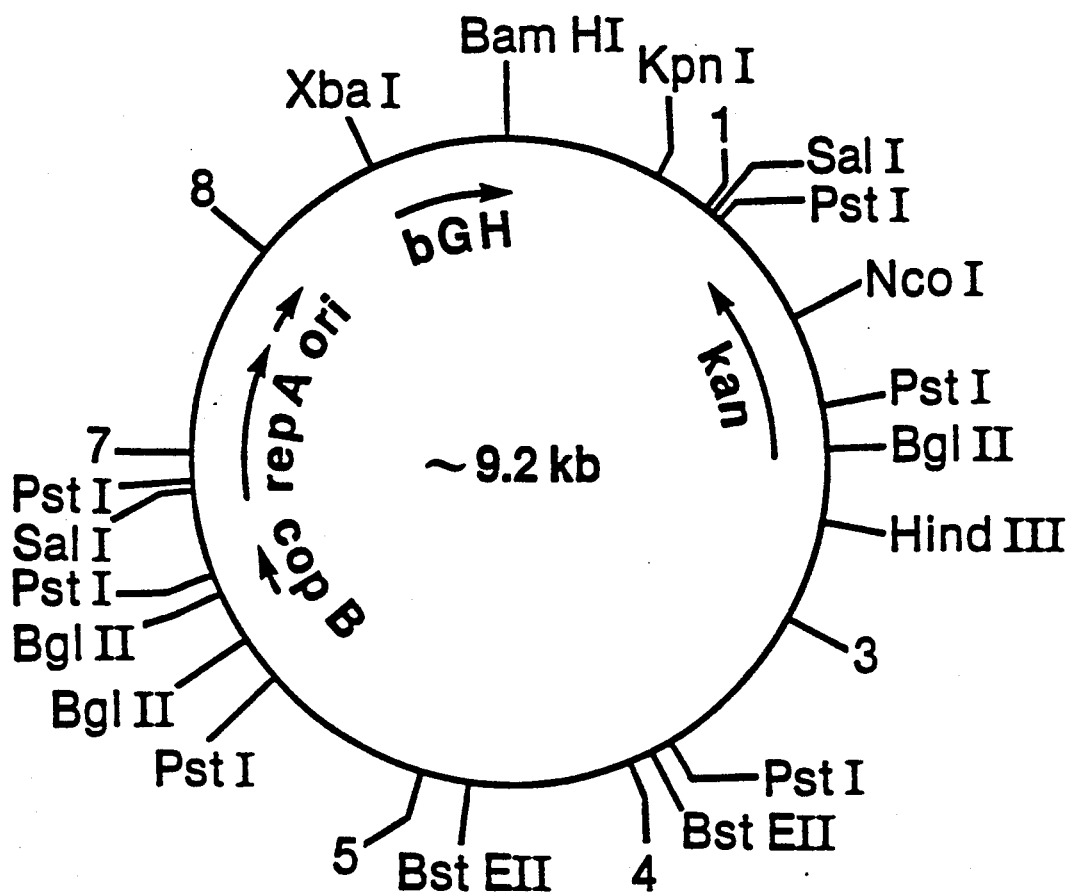
FIG. 10—Restriction site map of plasmid pCZ118.

Some of the resultant transformants, as conventionally shown by agarose gel electrophoresis (Maniatis et al., 1982) and other tests, contained only the desired ~9.2 kb plasmid (FIG. 10). Such a transformant, herein designated as *E. coli* K12 RV308/pCZ118, was selected, plated on TY agar containing appropriate antibiotics and then cultured using conventional microbiological techniques.

EXAMPLE 4

Construction of Plasmid pCZ145 and *E. coli* K12 RV308/pCZ145

A. Construction of the ~8.6 kb BamHI-XbaI Fragment of Plasmid pCZ118

The desired fragment was constructed in substantial accordance with the teaching of Example 2B except that plasmid pCZ118, rather than plasmid pNM789B, was used. The desired ~8.6 kb BamHI-XbaI restriction fragments were conventionally separated and isolated by agarose gel electrophoresis (Maniatis et al., 1982) and then dissolved in about 100 μl of TE buffer and stored at 0° C. for future use.

B. Construction of the ~0.6 kb BamHI-HgiAI Fragment of Plasmid pCZ101

The desired fragment was constructed in substantial accordance with the teaching of Example 2B except that plasmid pCZ101 and HgiAI restriction enzyme, rather than plasmid pNM789B and XbaI restriction enzyme, were respectively used. The desired ~0.6 kb BamHI-HgiAI restriction fragments were conventionally separated and isolated by agarose gel electrophoresis (Maniatis et al., 1982) and then dissolved in about 100 μl of TE buffer and stored at 0° C. for future use.

C. Construction of the DNA Linker Sequence

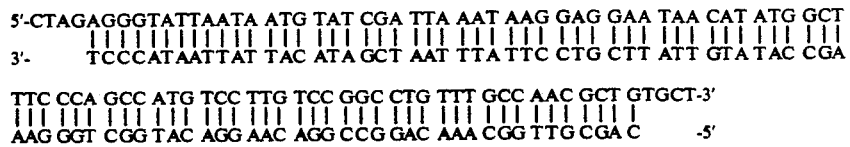

The desired linker sequence was conventionally synthesized by the modified phosphotriester method in substantial accordance with the teaching of Itakura et al., 1977 and Crea et al., 1978. The aforementioned synthesis method is also specifically illustrated in Example 1.

D. Ligation and Transformation

About 20 picomoles of the DNA linker of Example 4C, 1 μg of the plasmid pCZ118 ~10.2 kb BamHI-XbaI fragment and 0.5 μg of the plasmid pCZ101 ~0.6 kb BamHI-HgiAI fragment were ligated and the resultant plasmid used to transform *E. coli* K12 RV308 in substantial accordance with the teaching of Example 2D.

Figure 11:
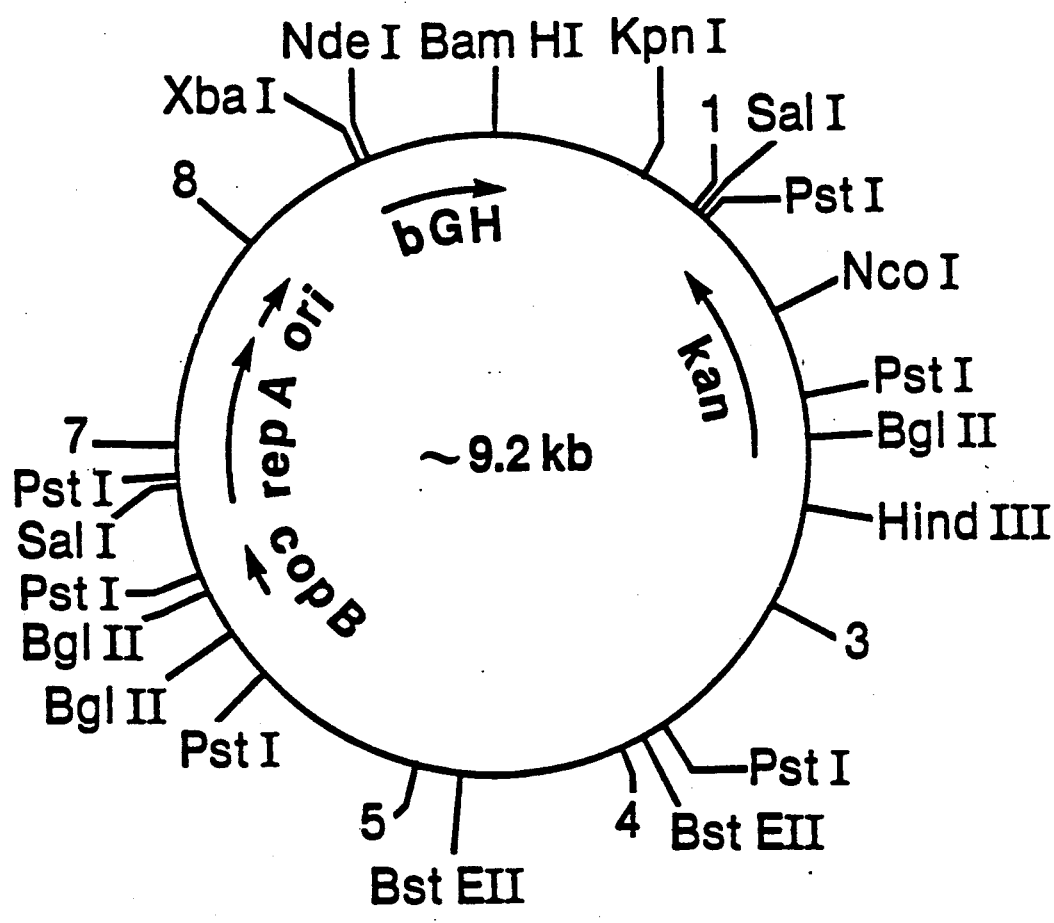
FIG. 11—Restriction site map of plasmid pCZ145.

Some of the resultant transformants, as conventionally shown by agarose gel electrophoresis (Maniatis et al., 1982) and other tests, contained only the desired ~9.2 kb plasmid (FIG. 11). Such a transformant, herein designated as *E. coli* K12 RV308/pCZ145, was selected, plated on TY agar containing appropriate antibiotics and then cultured using conventional microbiological techniques. The resultant cells were shown, by SDS gel electrophoresis, RIA and other tests, to express met-bGH at high levels Because plasmid pCZ145 contains a thermoinducible runaway replicon, maximum expression of met-bGH occurs at culture temperatures of about 37° C.

EXAMPLE 5

Construction of Plasmid pCZ149 and *E. coli* K12 RV308/pCZ149

A. Construction of the ~9.2 kb XbaI-NdeI Fragment of Plasmid pCZ145

About 5 μg of plasmid pCZ145 DNA in 50 μl of Hi Salt buffer was incubated with 10 units each of XbaI and NdeI restriction enzymes at 37° C. for about 1 hour. After the addition of 5 μl of 3M sodium acetate, pH 7.0, the DNA was precipitated with 3 volumes of 100% ethanol. This DNA was dissolved in 100 μl of TE buffer and stored at 0° C. for future use.

B. Construction of the DNA Linker Sequence

The desired linker sequence was conventionally synthesized by the modified phosphotriester method in substantial accordance with the teaching of Itakura et al., 1977 and Crea et al., 1978. The aforementioned synthesis method was also specifically illustrated in Example 1.

C. Ligation and Transformation

About 20 picomoles of the linker of Example 5B and 1 μg of the pCZ145 digest of Example 5A were ligated and the resultant plasmid was used to transform *E. coli* K12 RV308 in substantial accordance with the teaching of Example 2D.

Some of the resultant transformants, as conventionally shown by agarose gel electrophoresis (Maniatis et al., 1982) and other tests, contained only the desired ~9.2 kb plasmid. Such a transformant, herein designated as *E. coli* K12 308/pCZ149, was selected, plated on TY agar containing appropriate antibiotics and then cultured using conventional microbiological techniques. The resultant cells were shown, by SDS gel electrophoresis, RIA and other tests, to express met-bGH at high levels Because plasmid pCZ149 contained a thermoinducible runaway replicon, maximum expression of met-bGH occurred at culture temperatures of about 37° C.

EXAMPLE 6

Construction of Plasmid pCZ183 and *E. coli* K12 RV308/pCZ183

The desired constructions were made in substantial accordance with the teaching of Example 5 except the DNA linker sequence

```
5'- CTAGAGGGTATTAATAATCTATCGATTTAAATAAGGAGGAATAACA   -3'
       IIIIIIIIIIIIIIIIIIIIIIIIIIIIIIIIIIIIIIIIIIII
3'-        TCCCATAATTATTAGATAGCTAAATTTATTCCTCCTTATTGTAT-5'
``` was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ183, were plated on TY agar containing appropriate antibiotics and then conventionally cultured for subsequent production and isolation of plasmid pCZ183. The transformants were also shown, by SDS gel electrophoresis, RIA and other tests, to express met-bGH at high levels Because plasmid pCZ183 contained a thermoinducible runaway replicon, maximum expression of met-bGH occurred at culture temperatures of about 37° C.

EXAMPLE 7

Construction of Plasmid pCZ184 and *E. coli* K12 RV308/pCZ184

The desired constructions were made in substantial accordance with the teaching of Example 5 except the DNA linker sequence

```
5'-CTAGCGGATCCGCGATTAAATAAGGAGGAATAACA   -3'
     IIIIIIIIIIIIIIIIIIIIIIIIIIIIIIII
3'-       GCCTAGGCGCTAATTTATTCCTCCTTATTGTAT-5'
``` was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ184, were plated on TY agar containing appropriate antibiotics and then conventionally cultured for subsequent production and isolation of plasmid pCZ184. The transformants were also shown, by SDS gel electrophoresis, RIA and other tests, to express met-bGH at high levels Because plasmid pCZ184 contained a thermoinducible runaway replicon, maximum expression of met-bGH occurred at culture temperatures of about 37° C.

EXAMPLE 8

Construction of Plasmid pCZ149.1 and *E. coli* K12 RV308/pCZ149.1

The desired constructions were made in substantial accordance with the teaching of Example 5 except the DNA linker sequence

```
5'-CTAGCGATTAAATAAGGAGGAATAACA   -3'
     IIIIIIIIIIIIIIIIIIIIIIII
3'-       GCTAATTTATTCCTCCTTATTGTAT-5'
``` was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308.pCZ149.1, were plated on TY agar containing appropriate antibiotics and then conventionally cultured for subsequent production and isolation of plasmid pCZ149.1. The transformants were also shown, by SDS gel electrophoresis, RIA and other tests, to express met-bGH at high levels Because plasmid pCZ149.1 contained a thermoinducible runaway replicon, maximum expression of met-bGH occurred at culture temperatures of about 37° C.

EXAMPLE 9

Construction of Plasmid pCZ149.2 and *E. coli* K12 RV308/pCZ149.2

The desired constructions were made in substantial accordance with the teaching of Example 5 except the DNA linker sequence was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ149.2 were plated on TY agar containing appropriate antibiotics and then conventionally cultured for subsequent production and isolation of plasmid pCZ149.2. The transformants were also shown, by SDS 9el electrophoresis, RIA and other tests, to express met-bGH at high levels. Because plasmid pCZ149.2 contained a thermoinducible runaway replicon, maximum expression of met-bGH occurred at culture temperatures of about 37° C.

EXAMPLE 10

Construction of Plasmid pCZ149.3 and *E. coli* K12 RV308/pCZ149.3

The desired constructions were made in substantial accordance with the teaching of Example 5 except the DNA linker sequence

was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ149.3, were plated on TY agar containing appropriate antibiotics and then conventionally cultured for subsequent production and isolation of plasmid pCZ149.3. The transformants were also shown, by SDS gel electrophoresis, RIA and other tests, to express met-bGH at high levels. Because plasmid pCZ149.3 contained a thermoinducible runaway replicon, maximum expression of met-bGH occurred at culture temperatures of about 37° C.

EXAMPLE 11

Construction of Plasmid pCZ183.1 and *E. coli* K12 RV308/pCZ183.1

The desired constructions were made in substantial accordance with the teaching of Example 5 except the DNA linker sequence

was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ183.1, were plated on TY agar containing appropriate antibiotics and then conventionally cultured for subsequent production and isolation of plasmid pCZ183.1. The transformants were also shown, by SDS gel electrophoresis, RIA and other tests, to express met-bGH at high levels. Because plasmid pCZ183.1 contained a thermoinducible runaway replicon, maximum expression of met-bGH occurred at culture temperatures of about 37° C.

EXAMPLE 12

Construction of Plasmid pCZ183.2 and *E. coli* K12 RV308/pCZ183.2

The desired constructions were made in substantial accordance with the teaching of Example 5 except the DNA linker sequence

was substituted for the linker sequence of Example 5. The above-specified linker sequence was constructed in substantial accordance with the conventional procedure of Itakura et al., 1977 and Crea et al., 1978. The aforementioned synthesis method was also specifically illustrated in Example 1.

The desired transformants, herein designated as *E. coli* K12 RV308/pCZ183.2, were plated on TY agar containing appropriate antibiotics and then conventionally cultured for subsequent production and isolation of plasmid pCZ183.2. The transformants were also shown, by SDS gel electrophoresis, RIA and other tests, to express met-bGH at high levels Because plasmid pCZ183.2 contained a thermoinducible runaway replicon, maximum expression of met-bGH occurred at culture temperatures of about 37° C.

We claim:

1. A method for producing a polypeptide, the method comprising
   1) transforming a prokaryotic cell with a recombinant DNA expression vector which sequentially comprises
      a) a transcriptional activating sequence,
      b) a translational activating sequence selected from the group consisting of

-continued 5) 5'-CTAGCGGATCCGCGATTAAATAAGGAGG
   3'-    GCCTAGGCGCTAATTTATTCCTCC
          AATAACA -3'
          TTATTGTAT-5'

6) 5'-CTAGCGTTAACGCGATTAAATAAGGAGG
   3'-    GCAATTGCGCTAATTTATTCCTCC
          AATAACA -3'
          TTATTGTAT-5'

7) 5'-CTAGCGATTTAAATAAGGAGGAATAACA -3'
   3'-    GCTAAATTTATTCCTCCTTATTGTAT-5' and 8) 5'-CTAGCGGGATCCCGCGATTTAAATAAGG
   3'-    GCCCTAGGGCGCTAAATTTATTCC
          AGGAATAACA -3'
          TCCTTATTGTAT-5' wherein
A is deoxyadenyl,
G is deoxyguanyl,
C is deoxycytidyl,
T is thymidyl, and
c) a DNA sequence that codes for the functional polypeptide with a methionine as the first amino acid at the amino-terminus; subject to the limitation that sequences a and b are positioned for microbial expression of sequence c and
2) culturing the transformed cell under conditions suitable for gene expression.

2. The method of claim 1 in which the recombinant DNA expression vector is a plasmid.

3. The method of claim 1 in which the transcriptional activating sequence is selected from the group consisting of E. coli tryptophan, E. coli lipoprotein, E. coli lactose, bacteriophage λ P$_L$O$_L$, bacteriophage λ P$_R$O$_R$, Bacillus subtilis vegetative and Streptomyces azureus thiostrepton resistance transcriptional activating sequence.

4. The method of claim 1 in which the transcriptional activating sequence comprises one or more E. coli transcriptional activating sequences in tandem.

5. The method of claim 1 in which the transcriptional activating sequence is selected from the group consisting of E. coli tryptophan and E. coli lactose transcriptional activating sequence.

6. The method of claim 1 in which the polypeptide coding sequence is selected from the group consisting of sequences that code for bovine growth hormone, human growth hormone, human pre-growth hormone, procine growth hormone, mammalian growth hormone, avian growth hormone, human growth hormone releasing factor, bovine growth hormone releasing factor, porcine growth hormone releasing factor, human insulin A chain, human insulin B chain, human proinsulin, human and non-human interferon, urokinase, tissue plasminogen activator, interleukin I and interleukin II.

7. The method of claim 5 in which the polypeptide coding sequence is selected from the group consisting of sequences that code for bovine growth hormone, human growth hormone, human pre-growth hormone, procine growth hormone, mammalian growth hormone, avian growth hormone, human growth hormone releasing factor, bovine growth hormone releasing factor, porcine growth hormone releasing factor, human insulin A chain, human insulin B chain, human proinsulin, human and non-human interferon, urokinase, tissue plasminogen activator, interleukin I and interleukin II.

8. The method of claim 7 in which the polypeptide coding sequence codes for bovine growth hormone.

9. The method of claim 2 in which the plasmid is selected from the group consisting of pCZ149, pCZ183, pCZ184, pCZ149.1, pCZ149.2, pCZ149.3, pCZ183.1 and pCZ183.2.

10. The method of claim 9 in which the plasmid is pCZ149.

11. The method of claim 9 in which the plasmid is pCZ183.

12. The method of claim 9 in which the plasmid is pCZ184.

13. The method of claim 9 in which the plasmid is pCZ149.1.

14. The method of claim 9 in which the plasmid is pCZ149.2.

15. The method of claim 9 in which the plasmid is pCZ149.3.

16. The method of claim 9 in which the plasmid is pCZ183.1.

17. The method of claim 9 in which the plasmid is pCZ183.2.

18. The method of claim 1 in which the transformed prokaryotic cell is selected from the group consisting of E. coli, Bacillus and Streptomyces.

19. The method of claim 18 in which the transformed prokaryotic cell is E. coli.

20. The method of claim 17 in which the transformed prokaryotic cell is selected from the group consisting of E. coli K12 RV308/pCZ149, E. coli K12 RV308/pCZ183, E. coli K12 RV308/pCZ184, E. coli K12 RV308/pCZ149.1, E. coli K12 RV308/pCZ149.2, E. coli K12 RV308/pCZ149.3, E. coli K12 RV308/pCZ183.1 and E. coli K12 RV308/pCZ183.2.

21. The method of claim 20 in which the transformed prokaryotic cell is E. coli K12 RV308/pCZ149.

22. The method of claim 20 in which the transformed prokaryotic cell is E. coli K12 RV308/pCZ183.

23. The method of claim 20 in which the transformed prokaryotic cell is E. coli K12 RV308/pCZ184.

24. The method of claim 20 in which the transformed prokaryotic cell is E. coli K12 RV308/pCZ149.1.

25. The method of claim 20 in which the transformed prokaryotic cell is E. coli K12 RV308/pCZ149.2.

26. The method of claim 20 in which the transformed prokaryotic cell is E. coli K12 RV308/pCZ149.3.

27. The method of claim 20 in which the transformed prokaryotic cell is E. coli K12 RV308/pCZ183.1.

28. The method of claim 20 in which the transformed prokaryotic cell is E. coli K12 RV308/pCZ183.2.

* * * * *